US00PP18558P2

(12) United States Plant Patent
Harkness

(10) Patent No.: US PP18,558 P2
(45) Date of Patent: Mar. 4, 2008

(54) FLORIBUNDA ROSE PLANT NAMED 'HARGRACE'

(50) Latin Name: *Rosa hybrida*
Varietal Denomination: HARgrace

(75) Inventor: Robert B. Harkness, Le Tignet (FR)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 11/586,027

(22) Filed: Oct. 24, 2006

(51) Int. Cl.
*A01H 5/00* (2006.01)

(52) U.S. Cl. ..... Plt./143; Plt./146

(58) Field of Classification Search ..... Plt./143, Plt./146
See application file for complete search history.

(56) References Cited

U.S. PATENT DOCUMENTS

PP10,478 P * 7/1998 Harkness ..... Plt./141
PP15,334 P2 * 11/2004 Fryer ..... Plt./143

* cited by examiner

*Primary Examiner*—Wendy Haas
(74) *Attorney, Agent, or Firm*—Klarquist Sparkman LLP

(57) ABSTRACT

Floribunda rose plant having excellent flower form; high production of orange flowers; and dark, glossy foliage having good resistance to mildew and rusts.

1 Drawing Sheet

Figure 1:
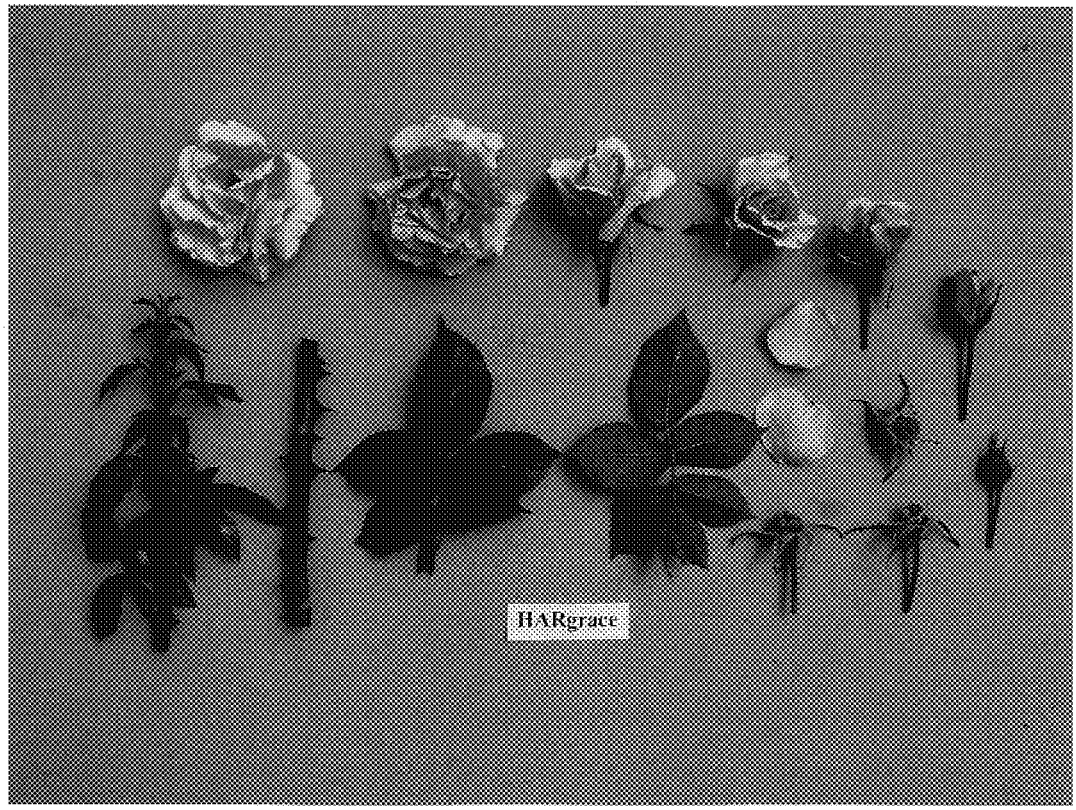

Genus and species: *Rosa hybrida.*
Variety denomination: 'HARgrace'.

ORIGIN OF THE INVENTION

The present invention relates to a new and distinct variety of a floribunda rose plant named 'HARgrace' which was originated by me by crossing the variety 'Silver Jubilee' (not patented), with the variety 'Dame of Sark' (not patented).

BACKGROUND OF THE INVENTION

The primary objective of this breeding was to produce a new floribunda rose variety having well formed blooms in sprays, to increase the disease resistance with the aim of developing a low maintenance rose and to improve the number of blooms by having the re-bloom cycle as speedy as possible.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Flower form is excellent like its female parent.
2. High flower production like the male parent.
3. Great flower color which is a blend of both parents.
4. Dark, glossy foliage like the female parent with the disease resistance of the male parent.

Asexual reproduction of this new variety by cuttings, as performed at Wasco, Calif., shows that the foregoing and all other characteristics and distinctions come true to form and are established and transmitted through succeeding propagations.

Comparison with Parents

'Silver Jubilee', the female parent, is a pink blend while 'HARgrace' is apricot to peach color. 'Silver Jubilee' hides its blooms while 'HARgrace' holds them above the plant. 'Silver Jubilee' has one bloom per stem while 'HARgrace' has large clusters of bloom. 'Dame of Sark', the male parent, is a red floribunda with some yellow on the petal reverse. 'Hargrace' is apricot to peach in color. 'Dame of Sark' frequently has distorted petals while 'HARgrace' is symmetrical in form.

Comparison with Similar Variety

'Hargrace' is similar to 'Southhampton' (unpatented), a marmalade-orange floribunda, which is more open and taller than 'HARgrace'. It is also similar to Easy Going ('HARflow') (U.S. Plant Pat. No. 10,478). Easy Going has golden-amber blooms while 'HARgrace' has apricot blooms. 'HARgrace' has larger sprays than Easy Going.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:
*Seed parent.*—'Silver Jubilee' (not patented).
*Pollen parent.*—'Dame of Sark' (not patented).

FLOWER

Observations made from January 2006 to October 2006 from plants commencing at two years of age grown in a garden environment at Wasco and Somis, Calif.

Blooming habit: Continuous.
Bud:
*Size.*—About 30 mm long and 20 mm in diameter when the petals start to unfurl.
*Form.*—The bud form is long, pointed ovoid.
*Color.*—When sepals first divide, bud color is Orange Group 28C. When half blown, the upper sides of the petals are Orange Group 26D on the outer two-thirds, the petal changing to Yellow-Orange Group 14C with a final 10 mm×10 mm section at the petal base of Yellow-Orange Group 14A, and the lower sides of the petals are Orange Group 28C on the outer two-thirds of the petal changing to Yellow-Orange Group 14C on the bottom one-third of the petal.
*Sepals.*—Color: Upper surface: Mainly Yellow-Green Group 146B with occasional Greyed-Red Group 182A and an overlay of Greyed-White Group 156D. Lower surface: Blend of Yellow-Green Group 144A and Greyed-Purple Red Group 178B. Length: 25–30 mm. Width: 8–10 mm. Shape: Subulate. Surface texture: Upper: Hoary. Lower: Smooth with few glands. There are three lightly appendaged sepals. There are two unappendaged sepals with glandular edges.
*Receptacle.*—Color: Yellow-Green Group 144A. Shape: Funnel. Size: Small, about 5 mm long×5 mm wide. Surface: Hairy.
*Peduncle.*—Length: Short, averaging about 3–5 cm. Surface: Glandular. Color: Blend of Yellow-Green Group 144A and Greyed-Red Group 182A. Strength: Stiff, slender.
Bloom:
*Size.*—Medium. Average open diameter is about 80 mm.
*Borne.*—In flat clusters of 5–9 blooms.
*Stems.*—Strength: Strong. Average length is about 30–40 cm with a diameter of 7–8 mm.
*Form.*—When first open: High centered. Permanence: Flattens.
*Petalage.*—Number of petals under normal conditions: 15–20.
*Color.*—The upper sides of the inner petals are Orange Group 26D on the outer two-thirds of the petal changing to Yellow-Orange Group 14C with a final color spot 10 mm×10 mm of Yellow-Orange Group 14A. The reverse sides of the inner petals are Orange Group 28C on the outer two-thirds of the petal changing to Yellow-Orange Group 14C on the inner one-third of the petal with a final 10 mm×10 mm Yellow-Orange Group 14A color spot. The major color on the upper sides is Orange Group 26D.
*Variegations.*—None observed.
*Discoloration.*—The general tonality at the end of the first day: Little change. At the end of the third day: Changing to Orange Group 27A with Yellow-Orange Group 14A at the base. Further aging: No further change.
*Fragrance.*—Moderate, sweet damask.
Petals:
*Texture.*—Thick, leathery.
*Surface.*—Smooth.
*Shape.*—Orbicular.
*Margin.*—Entire. Apex Shape: Obtuse. Base Shape: Rounded.
*Form.*—Tips slightly recurved.
*Arrangement.*—Imbricated.
*Petaloids.*—Number: 1–3. Color: Same as petals.
*Persistence.*—Petals drop off cleanly before drying.
*Lastingness.*—On the plant: Fair (about 6 days). As a cut flower: Fair (about 8 days).
Reproductive parts:
*Stamens.*—Number: 60–80. Length: 9–13 mm. Anthers: Length: 1 mm. Color: Greyed-Orange Group 163B. Arrangement: Regular around styles. Filaments: Color: Red Group 45D at base fading to Yellow-Orange Group 19A. Length: 8–12 mm Pollen: Color: Greyed-Orange Group N172C.
*Pistils.*—Number: 40–60. Length: 6–8 mm. Styles: Color: Bottom half, Green-Yellow Group 1C; top half Red Group 45B. Length: 1 mm. Stigmas: Color: Greyed-Orange Group 165C. Length: 5–7 mm.
*Hips.*—None observed.

PLANT

Form: Bush.
Growth: Vigorous, upright, branching.
Age at maturity: Two years.
Mature plant: Height: 80–90 cm. Width: 60–70 cm.
Rootstock: Own root.
Foliage: Number of leaflets on normal mid-stem leaves: 5 or 7.
*Size.*—Medium. About 120 mm long×90 mm wide.
*Quantity.*—Normal.
*Color.*—New foliage: Upper side: Greyed-Red Group 178B. Lower side: Greyed-Red Group 178B. Old foliage: Upper side: Green Group 139A. Lower side: Green Group 139B.
Leaflets:
*Size.*—About 45 mm long×25 mm wide.
*Shape.*—Ovate.
*Base shape.*—Rounded.
*Apex shape.*—Acuminate.
*Texture.*—Leathery, glossy.
*Edge.*—Serrated.
*Serrations.*—Single.
*Petiole.*—Color: Yellow-Green Group 146C.
*Petiole rachis.*—Color: Yellow-Green Group 146C. Underside: Rough with prickles and glands.
*Auricles.*—None.
*Stipules.*—Length: 13–15 mm; serrated.
*Disease resistance.*—Resistant to mildew and rust and susceptible to blackspot under normal growing conditions.
*Pest resistance.*—Not observed.
*Vein color.*—Yellow-Green Group 146C.
*Venation pattern.*—Reticulate.
Wood:
*New wood.*—Color: Greyed-Red Group 178B. Bark: Smooth.
*Old wood.*—Color: Yellow-Green Group 146A. Bark: Smooth.
Prickles:
*Quantity.*—On main canes from base: 12–15 per 15 cm of cane. On laterals from main canes: 12–15 per 15 cm of cane.
*Form.*—Hooked slightly downward.
*Length.*—8–10 mm.
*Color when young.*—Greyed-Red Group 178A.
*Color when mature.*—Greyed-Yellow Group 160A.

Small prickles:

*Quantity.*—On main stalks: None. On laterals: None.

Winter hardiness: Hardy to Zone 5.

I claim:

1. A new and distinct variety of rose plant of the floribunda class, substantially as herein shown and described, characterized particularly by its excellent flower form; high production of orange flowers; and dark, glossy foliage having good resistance to mildew and rusts.

* * * * *

UNITED STATES PATENT AND TRADEMARK OFFICE

CERTIFICATE OF CORRECTION

PATENT NO. : PP 18,558 P2
APPLICATION NO. : 11/586027
DATED : March 4, 2008
INVENTOR(S) : Harkness It is certified that error appears in the above-identified patent and that said Letters Patent is hereby corrected as shown below:

In the Specification:

Column 2, line 8, "'Hargrace'" should read -- 'HARgrace' --

Column 2, line 14, "'Hargrace'" should read -- 'HARgrace' --

Column 3, line 27, "8 10 mm." should read -- 8-10 mm. --

Column 4, line 10, "60 80" should read -- 60-80 --

Column 4, line 10, "9 13" should read -- 9-13 --

Column 4, line 14, "8 12 mm" should read -- 8-12 mm --

Column 4, line 16, "40 60" should read -- 40-60 --

Column 4, line 16, "6 8" should read -- 6-8 --

Signed and Sealed this

Twentieth Day of April, 2010

David J. Kappos

David J. Kappos
*Director of the United States Patent and Trademark Office*